United States Patent [19]

Melker et al.

[11] Patent Number: 5,328,480
[45] Date of Patent: Jul. 12, 1994

[54] VASCULAR WIRE GUIODE INTRODUCER AND METHOD OF USE

[75] Inventors: Richard J. Melker, Gainesville, Fla.; Frank J. Fischer, Jr., Bloomington, Ind.

[73] Assignee: Cook Incorporated, Bloomington, Ind.

[21] Appl. No.: 959,287

[22] Filed: Oct. 9, 1992

[51] Int. Cl.⁵ ............................................. A61M 5/178
[52] U.S. Cl. ..................................... 604/164; 604/53; 604/264; 604/284
[58] Field of Search ................. 604/164, 53, 158, 168, 604/170, 264, 284, 283, 280

[56] References Cited

U.S. PATENT DOCUMENTS

| | | | |
|---|---|---|---|
| 4,493,707 | 1/1985 | Ishihara | 604/164 |
| 4,613,517 | 9/1986 | Williams et al. | 427/2 |
| 4,808,156 | 2/1989 | Dean | 604/164 |
| 4,932,942 | 6/1990 | Maslanka | 604/164 |
| 4,935,008 | 6/1990 | Lewis | 604/164 |
| 4,957,484 | 9/1990 | Murtfeldt | 604/164 |
| 5,120,319 | 6/1992 | Van Heugten | 604/168 |
| 5,149,330 | 9/1992 | Brightbill | 604/264 |

*Primary Examiner*—John G. Weiss
*Attorney, Agent, or Firm*—Richard J. Godlewski

[57] ABSTRACT

Multi-lumen wire guide introducer and method of inserting a wire guide or the like into the introducer prior to positioning the introducer in a vessel of the vascular system of a patient. The multi-lumen wire guide introducer comprises a tubular member formed of a semi-rigid plastic material such as a radiopaque polytetrafluoroethylene with first and second adjacent lumens extending longitudinally therein. In one aspect, the tubular member includes a tapered outer surface extending proximally from the distal end of the member and centered about the first lumen. The second lumen includes an opening in the tapered outer surface of the tubular member for extending a wire guide therefrom and into the blood vessel. In another aspect, the tubular member has proximal and distal portions with a first lumen extending longitudinally therethrough. The proximal portion includes a second lumen extending longitudinally therein and communicating with the first lumen prior to the distal portion. A method for positioning the multi-lumen introducer in the blood vessel of a patient includes the steps of providing and inserting a hollow needle through the first lumen, providing and inserting a wire guide in the second lumen, inserting the needle and tubular member into the blood vessel of a patient, advancing the wire guide from the second lumen into the blood vessel, and removing the needle and tubular member from the blood vessel when the wire guide is in place.

10 Claims, 2 Drawing Sheets

VASCULAR WIRE GUIODE INTRODUCER AND METHOD OF USE

CROSS-REFERENCE TO RELATED APPLICATION(S)

This application is related to copending application Ser. No. 07/959,289, entitled "A Multiple Lumen Vascular Access Introducer Sheath" of the present inventors filed concurrently herewith and assigned to a common assignee.

TECHNICAL FIELD

This invention relates to vascular introducers for inserting wire guides and the like into the vascular system of a patient and, in particular, to a multi-lumen introducer and method of positioning a wire guide in the introducer prior to insertion of the introducer and wire guide into a vessel of the vascular system.

BACKGROUND OF THE INVENTION

Many medical procedures require that medical personnel gain percutaneous access to the vascular system of a patient. Percutaneous access is achieved when a wire guide is positioned in the lumen of a blood vessel for permitting a dilator and introducer sheath to be positioned thereover and introduced into the vessel lumen. One technique for gaining vascular access is the Seldinger technique, which requires holding a hollow bore needle in a vessel of the vascular system while inserting a wire guide therethrough. Once the wire guide is positioned in the vessel and the needle is removed, a dilator and sheath are positioned over the wire guide and inserted into the vessel lumen. A problem with this technique is that it requires that medical personnel performing the procedure have significant dexterity and experience in performing the technique. It is difficult to keep the needle positioned in the vessel lumen. If the position of the needle changes, it may extend into the connective tissue surrounding the vessel and cause trauma to the access site. Furthermore, if the needle is positioned in connective tissue and the medical person inserts the wire guide therethrough, the wire guide damages the connective tissue surrounding the vessel. As a result of injury to the access site, medical personnel will have to find another access site. However, some patients do not have another viable access site. Another problem with this technique is that the wire guide is thin, flexible, and smooth, therefore difficult and time consuming to manipulate and guide through the needle. While insertion is being attempted, blood is typically spurting out of the introducer needle and contaminating the surgical field. This is of particular concern in view of the HIV virus and AIDS. Still another problem with this technique is that the wire guide may be sheared off by the metal needle, leaving a piece of the wire guide in the patient's body. Wire guides with a J-shaped or increasingly flexible distal end are particularly susceptible to shearing.

Another technique for gaining percutaneous vascular access uses over-the-needle catheters. Using the over-the-needle technique, a needle with a catheter positioned thereover is positioned in a vessel lumen. The catheter is pushed over the needle into the vessel lumen, and the needle is removed. Then a wire guide is positioned through the catheter, which is less likely to shear off the wire guide than a metal needle. A problem with this technique is that, again, manipulation of the wire guide is difficult and time consuming. In emergency and critical care situations, time delays may be life threatening. Furthermore, the process of feeding the wire guide into the vessel lumen through the catheter can be interrupted by an emergency push of medication or fluid. When this happens, the wire guide has to be completely removed from the catheter. Then vascular access is attempted at another site, if another access site is viable, or delayed until the introduction of fluid can be stopped or interrupted long enough to reinsert the wire guide and position a dilator and sheath in the vessel. Another problem with this technique is that the over-the-needle catheter has a small diameter for being positioned over the needle. As a result, the lumen is too small for permitting the introduction of a large volume of fluid such as the amount required to treat a patient suffering from hypovolemic shock.

SUMMARY OF THE INVENTION

The foregoing problems are solved and a technical advance is achieved in an illustrative multi-lumen wire guide introducer and a method of positioning a wire guide in a lumen of the introducer prior to insertion of the introducer and wire guide into a vessel of the vascular system. The vascular wire guide introducer comprises a tubular member having first and second adjacent lumens extending longitudinally therein. The tubular member also has a tapered outer surface extending proximally from the distal end of the member and positioned with respect to the first lumen. The second lumen has an opening in the tapered outer surface for advantageously introducing a wire guide into a vessel after the tubular member has been inserted in the vessel over a hypodermic needle positioned through the first lumen. The introducer further comprises a hollow cannula such as a hypodermic needle having a flash back chamber positioned in the first lumen for introducing the needle and tubular member into the blood vessel of a patient.

The introducer further comprises a hub attached about the proximal end of the tubular member. The hub has a first passage communicating with the lumen of the tubular member which are substantially collinear. The hub further includes a second passage communicating with the second lumen. The second passage is inclined with respect to the first passage of the hub for side entry of the wire guide into the second lumen of the tubular member. The tubular member comprises a semi-rigid plastic material such as radiopaque polytetrafluoroethylene.

In another aspect of the vascular wire guide introducer, the tubular member has a distal and a proximal portion. The distal and proximal portions have a first lumen extending longitudinally therethrough. The proximal portion has the second lumen extending longitudinally therein and communicating with the first lumen prior to the distal portion.

The method of introducing a wire guide into a blood vessel of a patient comprises providing the tubular member of the vascular wire guide introducer having first and second lumens extending therein, providing and inserting a hollow needle through the first lumen, and providing and inserting a wire guide in the second lumen. The method further includes inserting a needle and tubular member in the blood vessel of a patient and advancing the wire guide in the second lumen into the blood vessel after the needle and tubular member have been inserted into the blood vessel. This advantageously eliminates the problem of medical personnel having to insert the wire guide into the hypodermic needle after the needle is inserted into the vessel with blood spurting therefrom.

The method further comprises the step of providing the tubular member with a tapered outer surface extending proximally from a distal end thereof, the second lumen having an opening in the tapered outer surface. The needle and tubular member are removed from the blood vessel after the wire guide has been advanced from the opening in the tapered outer surface into the blood vessel.

The method further includes the step of providing the tubular member with distal and proximal portions having the first member extending longitudinally therethrough. The proximal portion has the second lumen extending longitudinally therein and communicates with the first lumen prior to reaching the distal portion. In this embodiment, the needle is pulled back into the tubular member when the needle and tubular member are positioned in the blood vessel. The wire guide is advanced from the second lumen into the first lumen and then into the blood vessel. The tubular member and needle are then removed from the blood vessel after the wire guide has been advanced therein.

DETAILED DESCRIPTION

Figure 1:
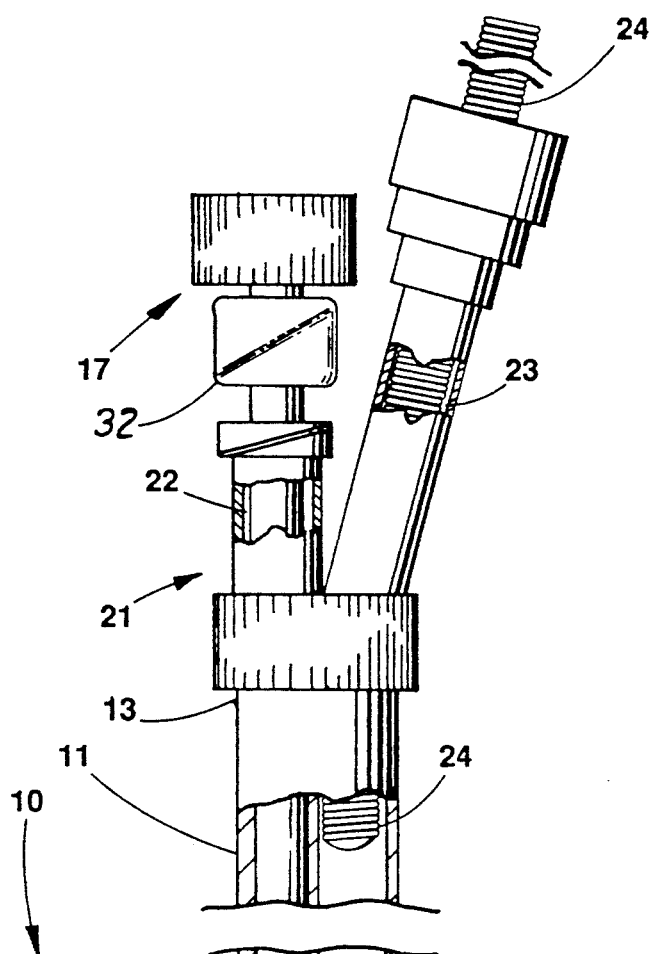
FIG. 1 depicts a partially sectioned longitudinal view of an illustrative vascular wire guide introducer of the present invention.

FIG. 1 depicts vascular wire guide introducer 10 with multiple lumens for positioning a wire guide in at least one of the lumens prior to inserting the introducer into the blood vessel of a patient. Vascular wire guide introducer 10 comprises tubular member 11 with distal end 12, proximal end 13, and adjacent lumens 14 and 15 extending longitudinally therein. First lumen 14 extends entirely therethrough for positioning hollow cannula 16 of, for example, commercially available hypodermic needle 17 with a flashback chamber 32 therein. Second lumen 15 provides for positioning wire guide 24 therein.

Tubular member 11 also has tapered outer surface 18 extending proximally from distal end 12. Tapered outer surface 18 is positioned with respect to first lumen 14 such as being centered about first lumen 14 so that second lumen 15 has opening 19 formed in the tapered outer surface. Tubular member 11 is formed of, for example, semi-rigid plastic material 20 such as a radiopaque polytetrafluoroethylene material, which permits tapering of the outer surface.

Introducer 10 further comprises hub 21 attached about proximal end 13 of tubular member 11. Hub 21 includes first passage 22 communicating with first lumen 14 of the tubular member. First passage 22 is substantially collinear with first lumen 14 for providing in-line insertion of a medical device such as a hypodermic needle therein. Hub 21 further includes second passage 23 communicating with second lumen 15 of the tubular member. Second lumen 23 is substantially inclined, or positioned at an angle, with respect to first passage 22 of the hub for providing insertion of a flexible medical instrument, such as wire guide 24, therethrough.

Figure 2:
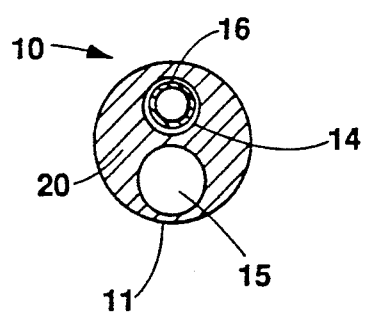
FIG. 2 depicts a cross-sectional view of the introducer of FIG. 1 along the line 2—2.

FIG. 2 depicts a cross-sectional view of tubular member 11 of introducer 10 of FIG. 1 along the line 2—2 with hollow cannula 16 positioned in first lumen 14. The wire guide of FIG. 1 is removed from second lumen 15.

Figure 3:
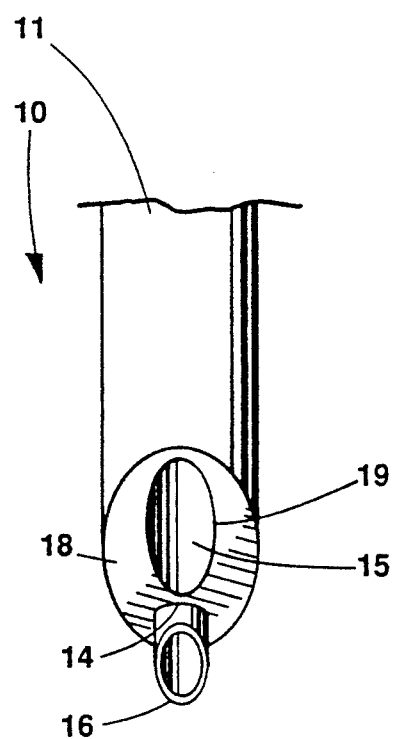
FIG. 3 depicts a partial, longitudinal view of the introducer of FIG. 1 along the line 3—3.

FIG. 3 depicts a partial, longitudinal view of tubular member 11 of introducer 10 of FIG. 1 along the line 3—3 with opening 19 of second lumen 15 positioned in tapered outer surface 18 thereof. Hollow cannula 16 extends from lumen 14 of tubular member 11.

By way of example, tubular member 11 of introducer 10 has approximately an 0.086" outside diameter and is 10 cm in length. First lumen 14 is approximately 0.030" in diameter, and second lumen 15 is approximately 0.037" in diameter. The septum of material positioned between the two lumens is approximately 0.003" thick at the minimum point. The minimum outer wall thickness of the tubular member is approximately 0.008". Tapered outer wall 18 extends proximally approximately 0.125" in length. Hollow cannula needle 17 has, for example, a 30 degree bevel in the distal end thereof and is approximately 0.028" in diameter. Wire guide 24 has an outside diameter of approximately 0.035".

Figure 4:
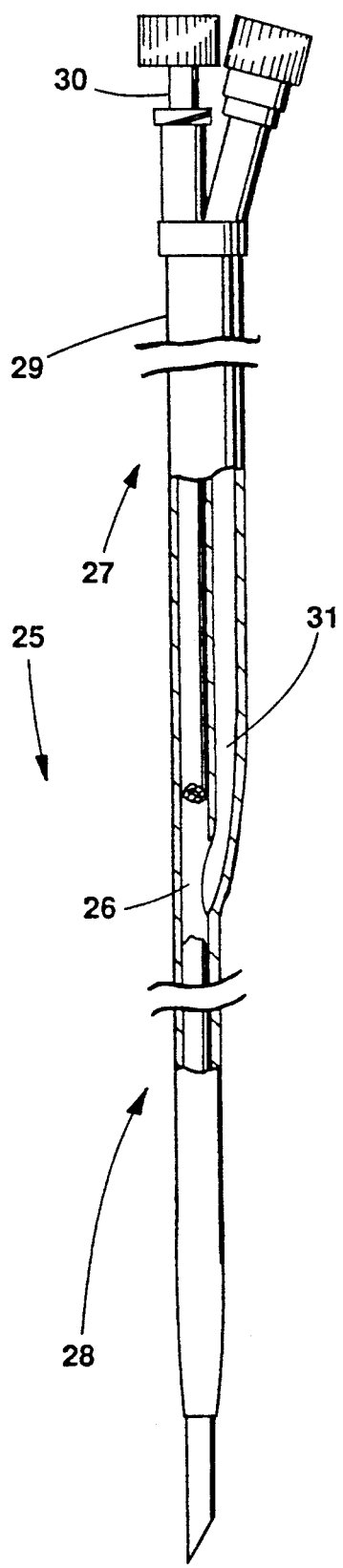
FIG. 4 depicts an alternative introducer of the present invention.

FIG. 4 depicts vascular wire guide introducer 25 with first lumen 26, which extends through proximal portion 27 and distal portion 28 of tubular member 29 for positioning hollow cannula 30 therein. Introducer 25 also has second lumen 31, which extends through proximal portion 27 for positioning a wire guide therein. Second lumen 31 communicates with first lumen 26 at a point proximal to distal portion 28 so that a wire guide is introduced into a blood vessel of a patient via first lumen 26. In this way, a wire guide is inserted into a blood vessel at precisely the site where the hypodermic needle was inserted into the patient.

A method of using introducer 10 for inserting a wire guide into a blood vessel of a patient comprises the initial step of providing a tubular member with first and second lumens extending therein such as tubular member 11. Then, a hollow needle such as a hypodermic needle is provided and inserted through first lumen 14 and a wire guide is provided and inserted through second lumen 15. Next, the needle and tubular member 11 of the introducer are inserted into a blood vessel of the patient. When vascular access is achieved and confirmed by a visible sample of blood in the flashback chamber of the hypodermic needle, the wire guide predisposed in second lumen 15 is advanced from the second lumen through opening 19 in tapered outer wall 18 into the blood vessel of the patient. The needle and tubular member are subsequently removed from the blood vessel.

Alternatively, introducer 25 (as depicted in FIG. 4) is used for introducing a wire guide into the vascular system of a patient. Once needle 30 and tubular member 29 of the introducer are inserted into the blood vessel, vascular access is confirmed by a visible sample of blood in the flashback chamber of the hypodermic needle. Then, the needle is pulled back from the tip of first lumen 26 to introduce the wire guide. The wire guide, which is predisposed in second lumen 31, is advanced from the second lumen into the first lumen. The wire guide exits the introducer via first lumen 26 about the distal end of the tubular member. After the wire guide is placed in the blood vessel, introducer 25 is removed from the patient.

It is to be understood that the above-described multi-lumen introducer is merely an illustrative embodiment of the principles of this invention and that other multi-lumen introducers may be devised by those skilled in the art without departing from the spirit and scope of this invention. It is contemplated that the tubular member comprises any biocompatible semi-rigid material. It is further contemplated that the first and second lumens are sized larger or smaller or have other cross-sectional shapes such as square, rectangular, oval, elliptical, crescent, or a combination thereof for accommodating various other clinical applications. It is also further contemplated that other multi-lumen introducers include more than two lumens.

What is claimed is:

1. A vascular wire guide introducer comprising:
a tubular member having a distal end, a proximal end, and first and second adjacent lumens extending longitudinally therein, and a cylindrical outer surface with a uniform outer diameter, said tubular member also having a tapered outer surface extending proximally from said distal end and centered with respect to said first lumen, said second lumen having an opening in said tapered outer surface.

2. The introducer of claim 1 further comprising a wire guide positioned in said second lumen.

3. The introducer of claim 2 further comprising a hollow cannula positioned in said first lumen.

4. The introducer of claim 3 wherein said cannula comprises a metal hypodermic needle having a flashback chamber.

5. The introducer of claim 3 further comprising a hub attached about said proximal end of said tubular member and having a first passage communicating with said first lumen of said tubular member, said first lumen and said first passage being substantially collinear.

6. The introducer of claim 5 wherein said hub further includes a second passage communicating with said second lumen, said second passage being inclined with respect to said first passage.

7. The introducer of claim 1 wherein said tubular member comprises a semi-rigid plastic material.

8. The introducer of claim 7 wherein said semi-rigid plastic material comprises a radiopaque polyetetrafluoroethylene material.

9. A method of introducing a wire guide into a blood vessel of a patient comprising the steps of:
providing a tubular member having first and second adjacent lumens extending longitudinally therein and a cylindrical outer surface with a uniform outer diameter;
providing said tubular member with a tapered outer surface extending proximally from a distal end thereof and centered with respect to said first lumen, said second lumen having an opening in said tapered outer surface;
providing and inserting a hollow needle through said first lumen;
providing and inserting a wire guide in said second lumen;
inserting said needle and said tubular member into a blood vessel of a patient; and
advancing said wire guide in said second lumen into said blood vessel when said needle and said tubular member have been inserted into said blood vessel.

10. The method of claim further comprising the step of removing said tubular member and said needle when said wire guide has been advanced into said blood vessel.

* * * * *